United States Patent [19]

Sia et al.

[11] Patent Number: 5,817,318

[45] Date of Patent: *Oct. 6, 1998

[54] SYNTHETIC PEPTIDES FOR AN HIV-1 VACCINE

[75] Inventors: Dwo Yuan Charles Sia; Pele Chong, both of Thornhill; Michel Klein, Willowdale, all of Canada

[73] Assignee: Connaught Laboratories Limited, North York, Canada

[ * ] Notice: The term of this patent shall not extend beyond the expiration date of Pat. No. 5,795,955.

[21] Appl. No.: 467,972

[22] Filed: Jun. 6, 1995

Related U.S. Application Data

[63] Continuation of Ser. No. 768,608, filed as PCT/CA90/00146, May 3, 1990, abandoned.

[30] Foreign Application Priority Data

May 3, 1989 [GB] United Kingdom .................. 8910145

[51] Int. Cl.$^6$ .................... A61K 39/21; A61K 39/00; A61K 39/38; C07K 1/00
[52] U.S. Cl. ..................... 424/208.1; 424/204.1; 424/188.1; 424/184.1; 530/350; 530/324; 530/325; 530/326
[58] Field of Search .............. 424/208.1, 188.1, 424/204.1; 530/350

[56] References Cited

U.S. PATENT DOCUMENTS

| | | | |
|---|---|---|---|
| 4,925,784 | 5/1990 | Crowl et al. | 435/5 |
| 5,013,548 | 5/1991 | Haynes et al. | 424/89 |

FOREIGN PATENT DOCUMENTS

| | | |
|---|---|---|
| 343132 | 5/1989 | European Pat. Off. . |
| 1179687 | 7/1989 | Japan . |
| 2188639 | 4/1986 | United Kingdom . |

OTHER PUBLICATIONS

Cohen, 1993, "Jitters Jeopardize AIDS Vaccine Trial", Science 262: 980–981.

Fox, 1994, "No Winners Against AIDS", Biotechnology 12:128.

Sternberg, et al, 1987, "Prediction of antigenic determinants . . ."FEBS Letters 218(2): 231–237.

*Primary Examiner*—Lynette F. Smith
*Attorney, Agent, or Firm*—Sim & McBurney

[57] ABSTRACT

The invention discloses the identification, characterization and use of a synthetic peptide, GPKEPFRDYVDRFYK (p24E), as a T-cell carrier for the appropriate assembly, with defined B-cell epitopes of the HIV-1 envelope protein, for the construction of potential synthetic vaccine candidates against HIV.

15 Claims, 1 Drawing Sheet

SYNTHETIC PEPTIDES FOR AN HIV-1 VACCINE

This is a continuation of application Ser. No. 07/768,608, filed as PCT/CA90/00146, May 3, 1990, now abandoned.

FIELD OF INVENTION

The present invention relates to the design and preparation of a synthetic peptide vaccine against acquired immunodeficiency syndrome (AIDS) caused by the human Immunodeficiency Virus (HIV). Particularly, the invention is related to the identification and characterization of a T-cell epitope of the core protein, p24, of HIV-1, and methodologies utilising this epitope to construct immunogenic oligopeptides with autologous (p24) and several heterologous (HIV proteins other than p24) B-cell epitopes capable of inducing effective immunity against HIV.

BACKGROUND OF THE INVENTION

AIDS is the ultimate result of infection with HIV, and there is currently no cure for the disease, so the development of an HIV-specific vaccine is urgently required. Previously, it has been proven that protective antibodies against a specific disease can be elicited by the administration of specific components of the organism causing the disease, rather than the whole organism that has been inactivated or has been attenuated to give a non-pathogenic strain. The envelope protein (gp160) of HIV-1 has been employed as a candidate vaccine against AIDS. Although it has been shown that this immunogen, prepared in a vaccinia vector, is capable of inducing virus neutralising antibodies, all vaccine trials failed to protect primates against challenge with wild HIV isolates. In addition, two regions of the protein gp160, encompassing residues 735–752 and 846–860, respectively, have been shown to suppress the normal human lymphocyte proliferative response to mitogens in animals immunized with these peptides conjugated to a carrier protein. This peptide-mediated immunosuppression may play an important role in the pathogenesis of the disease. These results also stress the need for a rational design of any synthetic vaccine against AIDS. To design the best candidate synthetic vaccine, very immunogenic viral B-cell neutralising epitopes (BE) containing a high degree of conserved sequence between viral isolates must be linked to potent T-helper cell determinants (THD) to elicit a strong and long-lasting cross-protective antibody response. Also, HIV-specific cytotoxic T-lymphocyte epitopes (CTL) should be included in the synthetic constructs to provide necessary cell-mediated immunity to HIV disease.

A specific and preferential spatial relationship between certain T- and B-cell epitopes may be necessary for tandem epitopes to be efficiently processed and immunogenic. Thus, it is important to determine whether T- and B-cell epitopes in a proposed designer vaccine are assembled in the optimal configuration so that both T- and B-cell memory can be elicited effectively and antibodies of the desired specificity produced. THD have been found not to be universal and are immunologically functional only when presented in association with the appropriate Major Histocompatibility Complex (MHC) class II antigens. There is a characteristic hierarchy of T-cell epitope dominance. Therefore, to develop a synthetic AIDS vaccine, it is important to identify the most potent THD of the various HIV gp160, gag, pol and other gene products. A number of THD and BE of the gp160 protein have been fully characterised and although the B- and T-epitopes of gag and pol proteins have been predicted by standard algorithms, the structure of these epitopes have yet to be determined experimentally. Recent studies have indicated that the gag gene products may play a crucial role in eliciting an immune response against HIV infection. Thus, clinical progression of AIDS is associated with a reduction of circulatory antibodies to the gag p24 protein and antibodies raised against an immunodominant gag p17 peptide are capable of inhibiting HIV-1 infection in vitro. Furthermore, Hepatitis B virus core THD have been shown to be more efficient than envelope THD in helping the induction of the antibody response to the S surface antigen. By analogy with the hepatitis B virus system, it was of interest to identify potent gag-THD in HIV. Using conventional structure prediction algorithms for T-cell and B-cell epitopes, we have identified and chemically synthesized a panel of potentially immunogenic gag peptides (Table I) and have extensively studied the immunological properties of one of them, p24E.

Published E.P. 0,273,716 describes the identification of short peptids of AIDS virus proteins which elicit T-cell immunity. The references disclose that certain segments of the gag region of the HIV genome are predicted as candidates for T-cell stimulation sites, including one identified as segment 284-309. There is no description of the synthesis of this segment nor any confirmation of immunological properties.

Published E.P. 0,284,383 discloses peptide sequences which immunologically mimic proteins encoded by the env and gag regions of LAV-2. A peptide derived from the a region of LAV-2 is designated 25-2-6 and is identified as comprising residues 274 to 316 and FIG. 2 shows the sequence for HIV-1. The peptide 25-2-6 is synthesized and antibody binding properties are shown.

However, neither reference recognizes the potential for combining T-cell and B-cell epitopes of HIV-1 in a candidate vaccine against HIV-1.

SUMMARY OF THE INVENTION

In accordance with one aspect of the present invention, the inventors have found a potent synthetic HIV-1 immunogen (HIV-1 p24) comprising gag-p24 tandem T- and B-cell epitopes. Inbred mouse strains primed with the free HIV-1-p24 peptide in complete Freund's adjuvant, and boosted with the same peptide in incomplete Freund's adjuvant elicited a strong secondary anti-HIV-1 p24 antibody response as judged by a peptide-specific enzyme immunoassay (EIA). The anti-peptide antibodies recognised the viral p24 protein in immunoblotting. In addition, the peptide presented in the appropriate MHC context was shown to be highly stimulatory for p24-specific murine T-cell lines.

The inventors have also demonstrated that the T-cell epitope of HIV-1-p24, p24E, can mediate an antibody response to heterologous B-cell determinants (envelope B-cell determinants, for example) and constructed several immunogenic chimeric p24/gp160 oligopeptides capable of inducing an anti-envelope antibody response.

The inventors have further shown that polarity of the T- and B-cell epitopes affects the immunogenicity of the chimeric peptides, and that the incorporation of a linker between the two epitopes can modulate the immunogenicity of the peptides.

DESCRIPTION OF INVENTION

Figure 1:
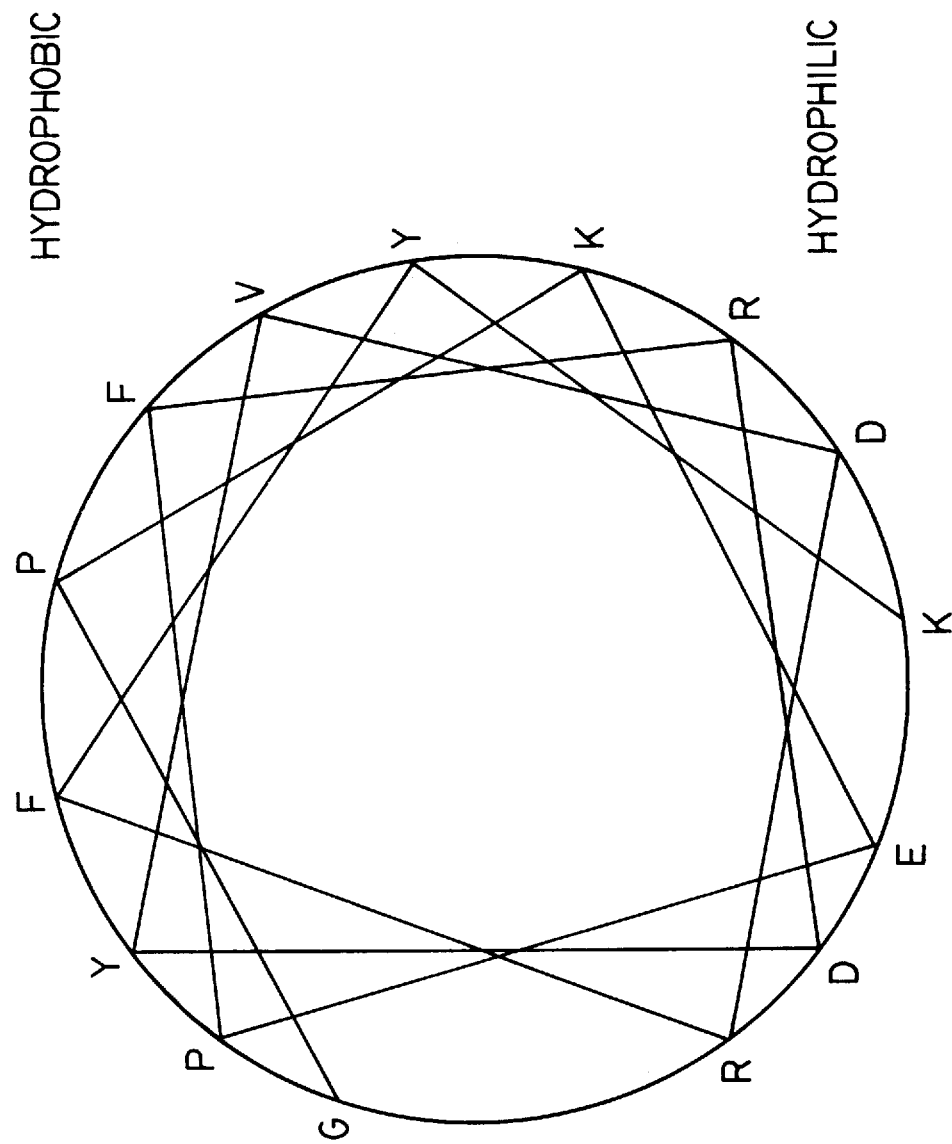
FIG. 1 is schematic representation of the structure of the p24E protein.

Two models have recently been proposed for the prediction of T-cell antigenic determinants on the basis of the primary sequence. It has been proposed (ref I.) that T-cell epitopes are likely to involve protein sequences that have a potential to adopt stable amphipathic α-helix conformations, such that hydrophilic residues are positioned on one side of the helix and hydrophobic residues lie on the other side. It has been independently observed that a primary sequence pattern occurs frequently in T-cell antigenic sites. This T-cell binding motif usually consists of a charged residue or a glycine followed by two or three hydrophobic residues followed by an hydrophilic residue (ref 2.).

Location of the potential T-cell epitopes of the HIV-I p24 protein has been predicted by structural algorithms (Table 1). The sequence GPKEPFRDYVDRFYK, of one of the predicted p24 T-cell epitopes, p24E, is very highly conserved in the various HIV-1 strains that have been isolated and likely has an amphipathic α-helix structure as shown in FIG. 1.

The results of the in vitro proliferation experiment demonstrating that p24E indeed contains a T-cell epitope are shown in Table 2. The p24-specific murine T-cell line, Tp241 was found to respond only to the synthetic peptide, p24E, but not to either TE1E or TB8 peptides which individually contain a partial sequence of p24E.

The T-cell carrier function of p24E was demonstrated by studying the immunogenicity of an unconjugated oligopeptide HIV-1-p24 encompassing p24E (residues 292–306), and a predicted p24 B-cell epitope, B (residues 307–316), of the gag protein, p24. HIV-1-P24 and B p24 peptides were injected separately in increasing amounts in complete Freund's adjuvant into five inbred mouse strains of different Major Histocompatibility Complex (MHC) haplotypes. The mice were boosted three weeks later with half the original amount of peptide in incomplete Freund's adjuvant. Sera were collected 9 days post-challenge and assayed for the presence of peptide-specific IgG antibodies.

Results of the enzyme immunoassay summarised in Table 3 indicate that the free p24 B peptide was not immunogenic at the three immunising doses (4, 20 and 100 ug) tested. However, this B-cell epitope became immunogenic when linked to the C-terminus of p24E (peptide HIV-1-p24). High titres of anti-HIV-1-p24 IgG were detected in the sera of immunised mice from four out of the five inbred strains, namely, Balb/c (H-2d), SWR/J (H-2q), C3H (H-2k and C57BL/6 (H-2b). The C57BL/6 and Balb/c mice appeared to be the best responders as judged by their high serum anti-peptide IgG titres (12,000 and 4,000, respectively), while the SWR/J and C3H strains with anti-HIV-1-p24 titres of 1 in 1,200 and the SJL/J strain with a titre of 1 in 150 were intermediate and poor responders to the peptide, respectively.

The immunogenicity of the B-cell epitope was found to depend on the polarity of B and p24E peptides . The oligopeptide in which the B-cell epitope, B is linked to the N-terminus of p24E was unable to induce an antibody response against its B-cell determinant (Table 3).

The specificity of the anti-HIV-1-p24 IgG antibodies was demonstrated by showing that a Balb/c (H-2d) anti-HIV-1-p24 antiserum reacted exclusively against p24 and not against other viral proteins, in EIA's using either recombinant p24 or gp41(DuPont) or gp160 (Repligen Corp.) as target antigens. The same antiserum also specifically recognized the viral p24 protein in immunoblotting using commercial HIV-1 Western blotting strips (Pan.Data Systems, Bio Rad). These results, therefore, demonstrate that p24E is a potent T-helper epitope (Th) capable of providing "immunological help" to induce the generation of antibody responses against autologous p24 B-cell epitopes in the absence of a foreign carrier protein.

In order to investigate whether the T-helper (Th) epitope, p24E, could also mediate an antibody response against heterologous B-cell determinants, we synthesized a chimeric oligopeptide, p24E-BE3 which contains a non-immunogenic B-cell epitope sequence BE3, encompassing amino acid residues 727–751 (LPTPRGPNRPEGIEEEGGERDRDRS) of the HIV-1 gp160 envelope protein (ref 3) linked in tandem to the C-terminus of p24E.

The five inbred mouse strains (Balb/c, SJL/J, A/J, C3H and C57BL/6) immunised with the free chimeric peptide following the protocol used for immunization with the HIV-1-p24 peptide were able to generate a secondary anti-envelope (BE3) antibody response as shown in Table 4. The highest anti-BE3 serum IgG titres (1 in 1,600) were obtained in Balb/c and C57BL/6 mouse strains immunized with 100 ug of p24E-BE3 peptide, suggesting that these two haplotypes are the best responders to the chimeric peptide.

We have introduced a spacer sequence between the T- and B-cell epitopes to modulate the immunogenicity of a chimeric peptide, BE3-p24E. Unlike in p24E-BE3, the BE3 sequence of the BE3-p24E peptide is located at the N-terminus of p24E. This BE3-p24E peptide was not, immunogenic in the five inbred mouse strains tested (Table 5). In contrast, the chimeric peptide, BE3-PP-p24E in which two proline residues (PP) have been inserted between the T and B-cell epitopes was immunogenic, and able to induce anti-BE3 antibody production in the five inbred mouse strains tested (SJL/J, A/J, C57BL/6, Balb/c and C3H). Collectively, the above results suggest that the enhancement of the immunogenicity of BE3 using p24E as a T-cell carrier is dependent on the polarity of the epitopes. The non-immunogenic form of the synthetic construct, BE3-p24E can be made immunogenic by inserting a linker, such as proline-proline, between the epitopes.

The p24E peptide was also used to enhance the immunogenicity of other heterologous B-cell epitopes. The chimeric peptides, ENV-PP-p24E and p24E-PP-ENV were synthesized using another HIV-1 B-cell epitope, ENV, encompassing the amino acid residues 256–273 (GIRPVVSTQLLLNGSLAE) of the envelope protein gp120(ref 4) linked in tandem to either the N- or C-terminus of p24E, respectively, via a proline-proline linker. The construct p24E-PP-ENV was found to be immunogenic in the five inbred strains examined as judged by the humoral response against the ENV peptide (Table 6). In contrast, ENV-PP-p24E was immunogenic in only three out of the five strains. These results confirm that the polarity of the B- and T-cell epitopes is critical in determining the immunogenidity of chimeric peptides. The carrier function of the p24E peptide was further assessed by studying the immunogenicity of another chimeric peptide, V3A-PP-p24E. The V3A sequence NTRKSIRIQRGPGRAFVTIG (residues 308–327) of the variable loop of HIV-1 gp 120, Which contains a major neutralising B-cell epitope (ref 5), is not immunogenic in inbred mice (Table 7). The V3A peptide was made immunogenic by being linked to the N-terminus of p24E via the proline-proline linker. The highest anti-V3A peptide IgG titre was measured in sera of STL/J mice immunised with V3A-PP-p24E.

The invention is further illustrated by the following examples

EXAMPLES

Methods of peptide synthesis, enzyme immunoassays (EIA) and other immunological testing procedures that are not explicitly described in this disclosure and Examples are amply reported in the scientific literature and are well within the scope of those skilled in the art.

Example I

This Example illustrates the synthesis of peptides. The oligopeptides shown in Table I were synthesized according to the amino acid sequence reported for the HIV/LAV isolate using the ABI (Applied Biosystems Inc) 430A peptide synthesizer. The solid-phase synthesis protocol was followed as described by the manufacturer except that addition of histidine was done by double coupling. The crude peptides were removed from the resin by treatment with hydrofluoric acid in the presence of anisole, thiocresol and dimethyl sulphide followed by precipitation with diethyl ether. The peptides were purified by reverse-phase high performance liquid chromatography (RP-HPLC) using a Vydac C4 column and an acetonitrile gradient in 0.1% trifluoracetic acid. Amino acid analyses showed that amino acid compositions of individual purified peptides were correct.

Example II

This Example illustrates the method used to demonstrate that the p24E peptide is a functional T-cell epitope.

Murine T-cell lines, specific for the peptide HIV1-p24, were generated according to a method similar to that described by Sia (ref 6). An optimal concentration of HIV-1-p24 peptide (100 ug/ml) was used to propagate the antigen-specific Balb/c T-cell lines in the presence of recombinant interleukin-2 (20 u/ml). The ability of the p24E peptide presented by syngeneic splenocytes to induce the proliferation of the T-cell lines in vitro as judged by a standard tritiated thymidine uptake assay clearly demonstrated that p24E contained a functional T-cell epitope (Table 2). In addition, the immunisation of Balb/c mice with the free p24E peptide emulsified in Freund's adjuvant did not elicit an anti-p24E antibody response.

Example III

This Example describes the protocol used to test the immunogenicity of the HIV-1-p24 peptide and chimeric oligopeptides.

Five inbred mouse strains of different MHC haplotypes, namely, Balb/c (H-2d), SJL/J (H-2s), A/J (H-2a), C3H (H-2k) and C57BL/6 (H-2b) were used for immunogenicity studies. Four mice from each strain were immunised with either 4, 20 or 100 ug of the free oligopeptide as follows. The animals received the given dose of the peptide in complete Freund's adjuvant (CFA) by the subcutaneous route; this was followed with a challenge-dose of half of the amount of the same peptide emulsified in incomplete Freund's adjuvant (IFA) three weeks later. Sera of the experimental animals collected on the 9th day post-challenge were assayed for peptide-specific IgG antibodies using a standard EIA.

Example IV

This Example illustrates the testing of anti-peptide antibodies using an Enzyme Immunoassay (EIA).

EIA for the detection of anti-HIV-1-p24 antibodies was performed by coating EIA plates (Maxisorp, NUNC, Denmark) with HIV-1-p24 in phosphate buffered saline (PBS, pH 7.0) at 1 ug per well. Absorption of the peptide was allowed to take place overnight at 4° C. The peptide solution was aspirated from the wells, and the plates were blocked by the addition of 300 ul 2% (w/v) of skimmed milk (Carnation, U.K.) per well. After 2 hr incubation at room temperature, the unbound peptide was removed by washing the plates three times with washing buffer [PBS, pH 7.0, containing 0.025% Tween 20 (Bio-rad Laboratories, Richmond, Calif.)]. A 3-fold dilution of each of the experimental serum sample starting at 1 in 50 was then made in PBS containing 0.1% skimmed milk, and 100 ul of the diluted serum was then added to each of the peptide-coated wells. Each dilution of serum samples was assayed in duplicate. Binding of the serum anti-HIV-1-p24 antibodies to the immobilized peptide was allowed to take place by incubating the plates for 1 hr at room temperature. The unbound antibodies were removed by washing the plates three times with washing buffer. One hundred ul of goat anti-mouse IgG antibody conjugated to horse-radish peroxidase (Jackson Lab.,) diluted 1 in 5,000 in washing buffer as recommended by the manufacturer, was then added to each wells to detect the specific binding of the anti-HIV-1-p24 IgG to the target peptide. After 1 hr of incubation at room temperature, the unbound antibody-conjugate was removed by washing the plates four times with the washing buffer. The amount of bound conjugate was assayed by the addition of 100 ul of a mixture of tetramethylbenzidine (TMB) and hydrogen peroxide (1 part of TMB to 9 parts of hydrogen peroxide). Colour development was allowed to take place at room temperature in the dark for 10–15 min., and arrested by the addition of 100 ul of 1N sulphuric acid. The optical densities of the enzyme reactions were read on a Titertek Multi Skan Spectrophotometer (MCC/340 model) at 450 nm. Results are shown in Table 3 and are expressed as mean reciprocal titres. The reciprocal titres for normal mouse sera, irrespective of the haplotypes, were always <50.

Example V

This Example further illustrates the detection of anti-HIV envelope peptide antibodies.

Anti-envelope peptide antibodies were detected in an EIA similar to that described above, with the following modifications. EIA plates were coated with streptavidine in PBS at 3 ug/well. After the plates were blocked with 2% skimmed milk, 0.1 ug of biotinylated envelope peptide (BE3, ENV or V3A) was then added to each of the streptavidine-coated wells. Binding of the biotinylated peptide to streptavidine was allowed to take place for 2 hr. at room temperature. Unbound peptide was removed by washing the plates three times with the washing buffer (PBS, pH 7.0, containing 0.25% Tween 20). Anti-envelope IgG activity was then assayed by adding 100 ul of the experimental sera serially diluted in PBS containing 1% skimmed milk, into each of the wells coated with biotinylated peptide bound to streptavidine. Binding of anti-envelope antibodies was then detected using an affinity-purified goat anti-mouse IgG antibody conjugated to horseradish-peroxidase as described in Example IV. Results were represented in Tables 4, 5, 6 and 7.

Example VI

This Example illustrates the biotinylation of peptides.

One hundred ul of a solution of NHS-biotin (10 mg NHS-biotin in 1 ml dimethylformamide [DMF]) and 0.2 ml of 1M sodium bicarbonate were added to 1 mg of peptide dissolved in 2 ml of either DMF or 6M guanidine hydrochloride in PBS, pH 7.5. The peptides were allowed to react with NHS-biotin for 2–6 hr at room temperature. After modification, the biotinylated peptides were purified by reverse phase HPLC or gel filtration chromatography.

Example VII

This example illustrates the use of the T-cell epitope, p24E as a T-cell carrier peptide.

Immunogenicity studies showed that the five inbred mouse strains (Balb/c, SJL/J, A/J, C3H and C57BL/6) immunized with the unconjugated chimeric peptide, p24E-BE3, using the protocol as described for the HIV-1-p24 peptide in Example III, were found to be able to generate a secondary anti-envelope peptide (anti-BE3) antibody response (Table 4).

Example VIII

This Example illustrates the use of a proline-proline linker to modulate the immunogenicity of chimeric peptides.

An immunogenicity experiment similar to that described in Example III was performed with the peptides BE3-p24E and BE3-PP-p24E which contained two proline residues between the T- and B-cell epitopes. Anti-BE3 antibodies were measured by EIA using biotinylated BE3 as the target antigen. Results are represented in Table 5.

Example IX.

This Example illustrates the use of p24E as a T-cell carrier for other heterologous B-cell epitopes.

An immunogenicity experiment similar to that in Example III was performed with the chimeric peptides, ENV-PP-p24E, p24E-PP-ENV and V3A-PP-p24E. Results are presented in Tables 6 and 7, respectively.

Example X

This Example illustrates the use of the immunoblotting technique.

Antibodies raised in mice against the synthetic peptides were tested for their immuno-specificity using the immunoblot technique. HIV-1 viral proteins immobilised on nitrocellulose strips were purchased from Pan Data System Inc. and Bio-rad and immunoblotting was performed according to the manufacturer's specification. Mice sera were assayed at 1 in 100 dilution.

REFERENCES

1. Delisi and Bersofsky, P.N.A.S., 82, 7048, (1985)
2. Rothbard and Taylor, EMBO, 7, 93, (1988)
3. Kennedy et al., Science, 231, 1556, (1986)
4. Ho et al., Science, 239, 1021, (1988)
5. Matsushita et al., J. Virology, 62(6), 2107, (1988)
6. Sia et al., Immunology, 51, 755, (1984)

TABLE I

Predicted T-Cell Epitopes in the Gag Gene Products of HIV-1

| Gag Gene Product | Peptide Name | Sequence | Strain Homology |
| --- | --- | --- | --- |
| p17 | p17A | EELRSLYNTVAT | 92% |
|  | p17B | DTKEALDKIEEEQNKSKKKA | 80% |
| p24 | p24A | ARTLNAWVKVVEEKAFSPEVIP | 85% |
|  | p24B | LKETINEEAAEWDRVHPVHAG | 80% |
|  | p24C | GQLREPRGSDIAGTTSTLQEQI | 90% |
|  | p24D | IPVGEIYKRWIILGLNKIVRMYSP | 80% |
|  | p24E | GPKEPFRDYVDRFYK | 85% |
|  | HIV1-p24 | p24E TLRAEQASQEV | 80% |
|  | p24F | LEEMMTACQGVGGPGHKARVLAEA | 95% |
|  | p24G | TETLLVQNANPDCKTILKALGPAA | 85% |
| p15 | p15A | ARNCRAPRKKGCWKCGKEGHQMKDC | 80% |

TABLE 2

Proliferative response of the Balb/c p24-specific T-cell line Tp241 to synthetic HIV peptides

| | | Proliferation [$^3$H-Tdr uptake], counts per minute | | | |
| --- | --- | --- | --- | --- | --- |
| Antigen | Sequence | 100 ug | 20 ug | 4 ug | 0.8 ug |
| p24 |  | 17,406 ± 2,412 | 19,592 ± 2,241 | 16,875 ± 1,943 | 6,217 ± 771 |
| p24E (p24) | GPKEPFRDYVDRFYK (292–306) | 5,216 ± 619 | 6,274 ± 572 | 2,612 ± 325 | 712 ± 81 |
| TE1E (p24) | GPKEPFRDY (292–300) | 412 ± 47 | 428 ± 32 | 311 ± 57 | 386 ± 41 |
| TB8 (p24) | DRFYKTLR (302–309) | 609 ± 79 | 416 ± 54 | 363 ± 30 | 261 ± 24 |
| BE3 (gp160) | LPTPRGPDRPEGIEEEGGERDRDRS (727–751) | 426 ± 48 | 368 ± 44 | 264 ± 23 | 296 ± 25 |
| Control |  | 248 ± 21 |  |  |  |
| Con A (5 ug/ml) |  | 61,727 ± 7,428 |  |  |  |

TABLE 3

Comparative immunogenicity studies of the HIV-1-p24 and B-24E peptides

Reciprocal anti-HIV-p24 IgG titre

| | | Dose | | | | | | | | |
| --- | --- | --- | --- | --- | --- | --- | --- | --- | --- | --- |
| Mouse | Haplo- | 4 ug | | | 20 ug | | | 100 ug | | |
| Strain | type | B | HIV-1-p24E | B-p24E | B | HIV-1-p24E | B-24E | B | HIV-1-p24E | B-p24E |
| Balb/c | d | <50 | 2,000 | <50 | <50 | 4,000 | <50 | <50 | 4,000 | 50 |
| SJL/J | s | <50 | 50 | <50 | <50 | 50 | <50 | <50 | 150 | 50 |
| SWR/J | q | <50 | <50 | <50 | <50 | 50 | <50 | <50 | 1,200 | <50 |
| C3H | k | <50 | <50 | <50 | <50 | 50 | <50 | <50 | 1,200 | 50 |
| C57BL/6 | b | <50 | 4,000 | <50 | <50 | 12,000 | 50 | <50 | 12,000 | 50 |

TABLE 4

Antibody Response to the Peptide p24E-BE3

| | | Reciprocal anti-BE3 peptide IgG titre | | |
|---|---|---|---|---|
| | | Dose | | |
| Mouse Strain | Haplotype | 4 ug | 20 ug | 100 ug |
| Balb/c | d | 50 | 400 | 1,600 |
| SJL/J | s | <50 | 100 | 100 |
| A/J | a | <50 | <50 | 400 |
| C3H | k | 100 | 400 | 400 |
| C57BL/6 | b | 50 | 50 | 1,600 |

TABLE 5

Studies on chimeric peptides BE3-p24E and BE3-PP-p24E

| | Reciprocal anti-BE3 peptide IgG titre | | | | | |
|---|---|---|---|---|---|---|
| | Anti-BE3-p24E | | | Anti-BE3-PP-p24E | | |
| Mouse Strain | 4 ug | 20 ug | 100 ug | 4 ug | 20 ug | 100 ug |
| Balb/c | <50 | <50 | <50 c) | 50 | 50 | 100 |
| SJL/J | <50 | <50 | <50 | 100 | 100 | 200 |
| A/J | <50 | <50 | <50 | 50 | 100 | 400 |
| C3H | <50 | <50 | <50 | 200 | 800 | 1,600 |
| C57BL/6 | <50 | <50 | <50 | <50 | <50 | 500 |

TABLE 6

Antibody response to the chimeric peptides ENV-PP-24E & p24E-PP-ENV

| | Reciprocal anti-ENV peptide IgG Titre | | | | | |
|---|---|---|---|---|---|---|
| | ENV-PP-p24E | | | p24E-PP-ENV | | |
| Mouse Strain | 4 ug | 20 ug | 100 ug | 4 ug | 20 ug | 100 ug |
| Balb/c | ND | <50 | 50 c) | <50 | 50 | 100 |
| SJL/J | ND | 50 | 1,600 | <50 | <50 | 100 |
| A/J | ND | <50 | <50 | <50 | <50 | 800 |
| C3H | ND | <50 | <50 | <50 | 100 | 400 |
| C57BL/6 | ND | 50 | 50 | 400 | 3,200 | 3,200 |

TABLE 7

Immunogenicity of the oligopeptides V3A and V3A-PP-P24E

| | Reciprocal anti-V3A peptide IgG titre | | | |
|---|---|---|---|---|
| | Dose | | | |
| | 20 ug | | 100 ug | |
| Mouse Strain | V3A | V3A-PP-p24E | V3E | V3A-PP-p24E |
| SJL/J | <50 | 800 | <50 | 800 |
| SWR/J | <50 | 50 | <50 | 100 |
| | <50 | <50 | <50 | <50 |
| A/J | <50 | 50 | <50 | 50 |

What is claimed is:

1. A synthetic chimeric immunogenic peptide capable of eliciting HIV specific-antibodies, said synthetic peptide having the amino acid sequence of a functional T-cell epitope of the gag protein of HIV-1 linked to the amino acid sequence of a B-cell epitope of an envelope or gag protein of HIV-1 to provide an enhanced immune response to said B-cell epitope.

2. The peptide of claim 1 wherein the T-cell epitope has the amino acid sequence GPKEPFRDYVDRFYK (p24E) or GPKEPFRDYVDRFYKTLRAEQASQEV (HIV-1-p24).

3. The peptide of claim 2 wherein the B-cell epitope is a B-cell epitope of the gag protein linked to the C-terminus of the amino acid sequence of the T-cell epitope (p24E).

4. The peptide of claim 2 wherein the B-cell epitope is the BE3 sequence encompassing amino acid residues 727 to 751 of the HIV-1 envelope protein attached to the C-terminus of the amino acid sequence of the T-cell epitope (p24E) by a linker sequence.

5. The peptide of claim 2 wherein the B-cell epitope is a B-cell epitope linked to the C- or N-terminus of the amino acid sequence of the T-cell epitope (p24E) by a linker sequence.

6. The peptide of claim 5 wherein the linker sequence is PP.

7. The peptide of claim 6 wherein the B-ell epitope comprises BE3 connected to the N-terminus of the amino acid sequence of the T-cell epitope (p24E).

8. The peptide of claim 6 wherein said B-cell epitope comprises the ENV sequence encompassing the amino acid residues 256 to 273 of the HIV-1 envelope protein.

9. The peptide of claim 6 wherein the B-cell epitope comprises the V3A sequence encompassing the amino acid residues 308 to 327 of the variable loop of HIV-1 gP120 protein connected to the N-terminus of the amino acid sequence of the T-cell epitope (p24E).

10. An immunogenic composition, comprising, as the active component thereof, a synthetic chimeric immunogenic protein having the amino acid sequence of a T-cell epitope of the gag protein of HIV-1 linked to the amino acid sequence of a B-cell epitope of an envelope or gag protein of HIV-1.

11. The immunogenic composition of claim 10, wherein the T-cell epitope has the amino acid sequence GPKEPFRDYVDRFYK (p24E) or GPKEPFRDYVDRFYKTLRAEQASQEV (HIV-1- p24).

12. The immunogenic composition of claim 10 wherein the B-cell epitope is the BE3, ENV or V3A amino acid sequence.

13. The immunogenic composition of claim 12 wherein the B-cell epitope is joined to the C-terminus of the T-cell epitope.

14. The immunogenic composition of claim 12 or 13, wherein the B-cell epitope is joined to the C-terminus of the T-cell epitope by a linker sequence.

15. The immunogenic composition of claim 10, wherein the B-cell epitope is the BE3, ENV or V3A amino acid sequence joined to the T-cell epitope by a linker sequence comprising PP.

* * * * *